United States Patent [19]
Tu et al.

[11] Patent Number: 6,096,033
[45] Date of Patent: Aug. 1, 2000

[54] MEDICAL DEVICE HAVING ULTRASONIC ABLATION CAPABILITY

[76] Inventors: Hosheng Tu; Lily Chen Tu, both of 2151 Palermo, Tustin, Calif. 92782

[21] Appl. No.: 09/119,201

[22] Filed: Jul. 20, 1998

[51] Int. Cl.⁷ .................................................. A61B 17/39
[52] U.S. Cl. .................................. 606/31; 606/41; 606/47; 606/169; 601/2; 128/898; 607/102
[58] Field of Search .............................. 606/41, 45, 46, 606/47, 48, 169, 170, 171, 178, 27, 29, 31; 601/2–4, 50, 51, 54; 604/22; 607/116, 119, 102; 128/298

[56] References Cited

U.S. PATENT DOCUMENTS

| | | |
|---|---|---|
| 5,295,484 | 3/1994 | Marcus et al. ..................... 128/660.03 |
| 5,606,974 | 3/1997 | Castellano et al. ................ 128/662.06 |
| 5,674,191 | 10/1997 | Edwards et al. ........................... 604/22 |
| 5,895,356 | 4/1999 | Andrus et al. ........................... 600/439 |
| 5,906,628 | 5/1999 | Miyawaki et al. ...................... 606/169 |
| 5,944,737 | 8/1999 | Tsonton et al. .......................... 606/169 |
| 5,948,009 | 9/1999 | Tu .......................................... 606/169 |

*Primary Examiner*—Linda C. M. Dvorak
*Assistant Examiner*—David Ruddy

[57] ABSTRACT

A medical device for treating the uvula or airway obstructions by reducing the mass of cellular tissues, wherein a plurality of elongate tubular shafts comprises at least one ultrasonic transducer means disposed at its distal end portion of each shaft, an ultrasonic energy generating means, and a means for generating vibration at the distal section of the tubular element to effect the ablation having an additional vibrational massage therapy for the tissues.

4 Claims, 8 Drawing Sheets

MEDICAL DEVICE HAVING ULTRASONIC ABLATION CAPABILITY

The present invention generally relates to an improved medical device and methods for treating tissues, and more particularly, to such a medical device and methods for treating the uvular tissues and/or airway obstructions in a patient by delivering ultrasonic energy to the lesion sites in association with pressure therapy.

BACKGROUND OF THE INVENTION

The methods of the destruction of cellular tissues in situ has been used in the treatment of many diseases, or as an adjunct to surgical removal procedures. One method used requires heating the tissues, and causing them to shrink and tighten. It is often less traumatic than surgical procedures and may be the only alternative method, wherein other procedures are unsafe, complicate, or expensive. Ablative treatment devices have an advantage because of using a destructive energy that is rapidly dissipated and reduced to a non-destructive level by conduction and convection, to forces of circulating fluids and other natural processes.

Devices using microwave energy, radiofrequency energy, ultrasonic energy, cryogenic means, laser energy, and tissue destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the area of treatment, and applying energy diffusely through the duct wall into the surrounding tissues in the targeted directions.

Of particular interest to the present invention are ultrasonic energy therapeutic protocols, which have been proven to be highly effective. The traditional radiofrequency ablation provides therapeutic energy by heat conduction while the ultrasonic ablation can provide a deeper energy penetration. By heating the tissues, and causing them to shrink and tighten, the excess mass of tissue can be reduced to clear the air passageway. Ultrasonic energy, when coupled with a temperature control mechanism, can be supplied to the device-to-tissue contact site and deep into the tissue under precisely to obtain the desired tissue treatment. Ultrasonic energy is conveyed to the tissue by heat conduction and penetration.

To be more efficient in ultrasonic energy ablation, an ultrasonic transducer means with a vibration capability can be used to simultaneously deliver the massage therapy to the target tissues. The electric toothbrush with vibration has been disclosed in the following patents: Suyama in U.S. Pat. No. 4,944,296, Ng in U.S. Pat. No. 5,283,921, Hwang in U.S. Pat. No. 5,381,576, Okada in U.S. Pat. No. 5,421,726, Mei in U.S. Pat. No. 5,617,603, and Hahn in U.S. Pat. No. 5,651,157. All the above patents disclose the advantage of an electric toothbrush with vibration. However, they do not teach using an ablation means with vibration capability to treat the tissues for therapeutic purpose.

On the other hand, Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissues point, it is not disclosed that the particular needle electrode could possibly combine pressure therapy and ultrasonic energy for proper contact with the target tissues. The "pressure therapy" is defined in this invention as applying appropriate pressure onto the tissues by a medical device.

Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula and RF energy is applied to the uvula tissues to cause internal lesions. Edwards et al. does not disclose a catheter to ablate tissues, having the capability for delivering ultrasonic energy and pressure therapy for deep tissue treatment.

Marcus et al. in U.S. Pat. No. 5,295,484 and Castellano et al. in U.S. Pat. No. 5,606,974 teach a catheter system having ultrasonic device for intracardiac ablation of arrhythmias. However, neither discloses a medical device having ultrasonic energy and pressure/vibrational therapy to treat the tissues effectively.

Therefore, there is a need for an improved medical device and methods using the ultrasonic energy to treat uvular, airway obstructions, polyps, or tumors, while applying pressure and/or vibrational massage therapy.

SUMMARY OF THE INVENTION

In general, it is an object of the present invention to provide a method and an improved medical device for generating heat, to treat the uvula, airway obstructions, or other cellular tissues. It is a second object of the present invention to provide a medical device so that vibrational massage therapy can be applied to the uvula site, or the target cellular tissues, for intimate contact. It is another object of the present invention to provide a device utilizing ultrasonic transducer means for tissue treatment. It is still another object of the present invention to provide a method and a device for monitoring the temperature of the medical device, and to control the temperature by utilizing a temperature control mechanism and/or algorithm. The location of the temperature sensor means is preferably at the proximity of the ultrasonic transducer means of the medical device. It is still another object of this invention to provide a method and a device for treating uvula or cellular tissues in a patient by applying appropriate pressure to the tissues ("pressure therapy" as defined in this invention).

Briefly, heat is generated by supplying a suitable energy source to a device, that is comprised of a plurality of energy delivery or electrode means, in contact with the body tissues. A suitable energy source may consist of radiofrequency energy, microwave energy, ultrasonic energy, alternating current energy, or laser energy. The energy can be applied to the uvula or cellular tissues through the energy delivery or electrode means. A DIP (dispersive indifferent pad) type pad or electrode, that contacts the patient, is connected to the Indifferent Electrode Connector on the RF or ultrasonic energy generator. When using an alternating current as the energy input, the generator should be grounded to avoid electrical interference. Heat is controlled by the power of the ultrasonic energy delivered and by the delivery duration. The standard ultrasonic energy generator means, and its applications through the ultrasonic transducer means, to a patient are well known for those who are skilled in the art.

In summary, the present invention comprises at least one ultrasonic transducer mounted on a distal end portion of a device. The ultrasonic transducer may be a single crystal transducer or a phased array crystal transducer. Ultrasonic transducers adapted for use in the invention are those capable of generating frequencies in the 1–40 MHz range under an applied electrical energy of 1 watt or above. Ultrasonic transducers are typically composed of relatively brittle piezoelectric crystalline material that is somewhat fragile. The ultrasonic transducers may be manufactured in different shape and size. In one embodiment, for energy deep penetration purposes, the ultrasonic transducer has a sharp needle-like end to effect the "pressure therapy". The ultrasound transducer further comprises ultrasound crystals adapted to generate at least one of focused ultrasound energy or diffused ultrasound energy.

In an optional embodiment, means for generating vibration at the distal section comprises a motor mounted in the cavity of the handle, which has a rotatable motor shaft, an elongated connecting shaft having a first end, to which the distal end portion having at least an ultrasonic transducer is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the device comprises a plurality of "clamping members means", wherein the clamping member means is composed of a slidable clamp-type that is meant to slide, longitudinally, on a shaft or bar. A pair of the clamping members means clamps the target tissue from the tissue's opposite sides with proper pressure. The clamping members means is generally selected from the group of sliding head bar clamp fixtures, deep throat bar clamp fixtures, threadless bar clamp fixtures, or the like.

In one optional embodiment, the device is leak-proof so that the therapeutic agent, in either fluid phase or gel phase, can be diffused under a positive pressure to flow inside the lumen of the medical device from its proximal end to the distal end. The fluid is vented through an optional opening at the proximity of the electrode to effect the therapeutic purpose.

The method and medical device of the present invention has several significant advantages over other known systems or techniques to treat the uvula, airway obstructions, tumors, or polyps. In particular, the device system comprising the clamping member means, using ultrasonic energy as a heat source, in this invention and simultaneously applying pressure therapy to the tissues, results in a more efficient therapeutic effect, which is highly desirable in its intended application on the uvula or on other medical ablation applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
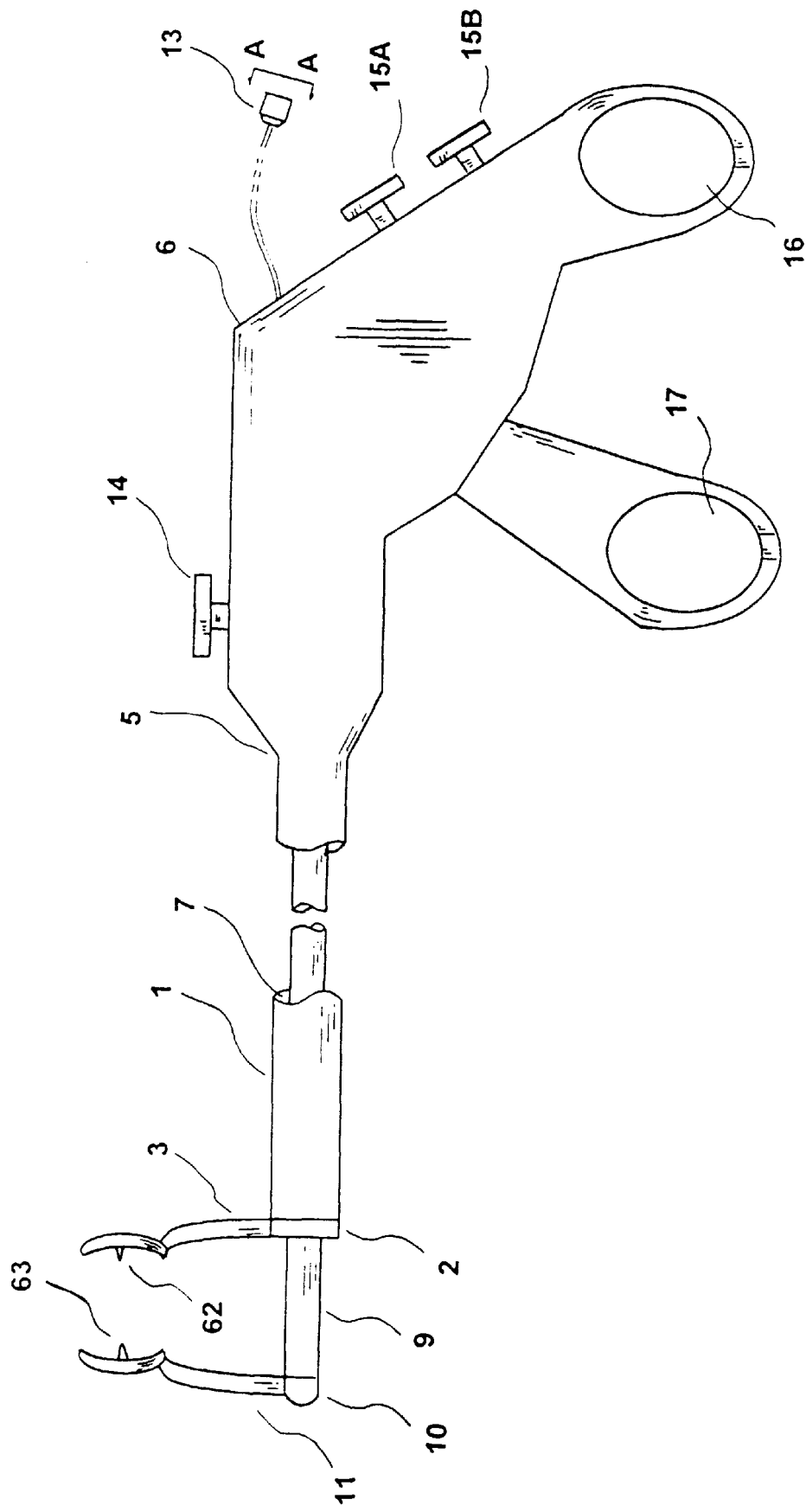
FIG. 1 is an over-all view of the medical device, comprising a plurality of ultrasonic transducer means having a clamp-type fixture, constructed in accordance with the principles of the present invention.

Referring to FIGS. 1 to 8, what is shown is an embodiment of the medical device system, comprising simultaneously applying ultrasonic energy and applying a pressure therapy to treat the uvula, airway obstructions, polyps, or other cellular tissues of a patient. As shown in FIG. 1, the medical device in the form of an elongate tubular assembly comprises a first elongate tubular shaft 1, on which thereof a first clamp means 3 having at least one ultrasonic transducer 62 is mounted on a distal end portion 2, an electrical conductor 4 passing through the shaft I and connected to the first ultrasonic transducer 62, and mounted on a proximal end portion 5 of the shaft 1 to a handpiece 6 of the device, wherein the first elongate tubular shaft 1 has at least a lumen 7 extending between the distal end portion 2 and the proximal end portion 5, and wherein the handpiece 6 has a cavity 8.

A second elongate tubular shaft 9 is located within the lumen 7 of the first elongate tubular shaft 1, the second elongate tubular shaft 9, on which thereof a second clamp means 11 having at least one ultrasonic transducer 63 is mounted on a distal end portion 10, an electrical conductor 12 passing through the shaft 9 and connected to the second ultrasonic transducer 63, and mounted on a proximal end portion of the shaft 9 to the handpiece 6 of the device, wherein the second elongate tubular shaft 9 is moveable longitudinally relative to the first elongate tubular shaft 1. A connector 13 is connected to the proximal end of the handpiece 6.

A securing mechanism 14 is positioned at a convenient location on the handpiece 6 to firmly secure the second elongate tubular shaft 9 in relation to the first elongate tubular shaft 1. The ultrasonic energy is supplied from an external ultrasonic energy generating means (not shown) to either the first ultrasonic transducer 62, the second ultrasonic transducer 63, or to both ultrasonic transducers through electrical conductors 4 and/or 12. One on-off control knob 15A or 15B is used to control each of the ultrasonic energy deliveries to the ultrasonic transducer 62 or 63. The handpiece 6 has a thumb holder 16 and a finger holder 17 to guide the device to the appropriate location of the targeted tissue site.

Figure 2:
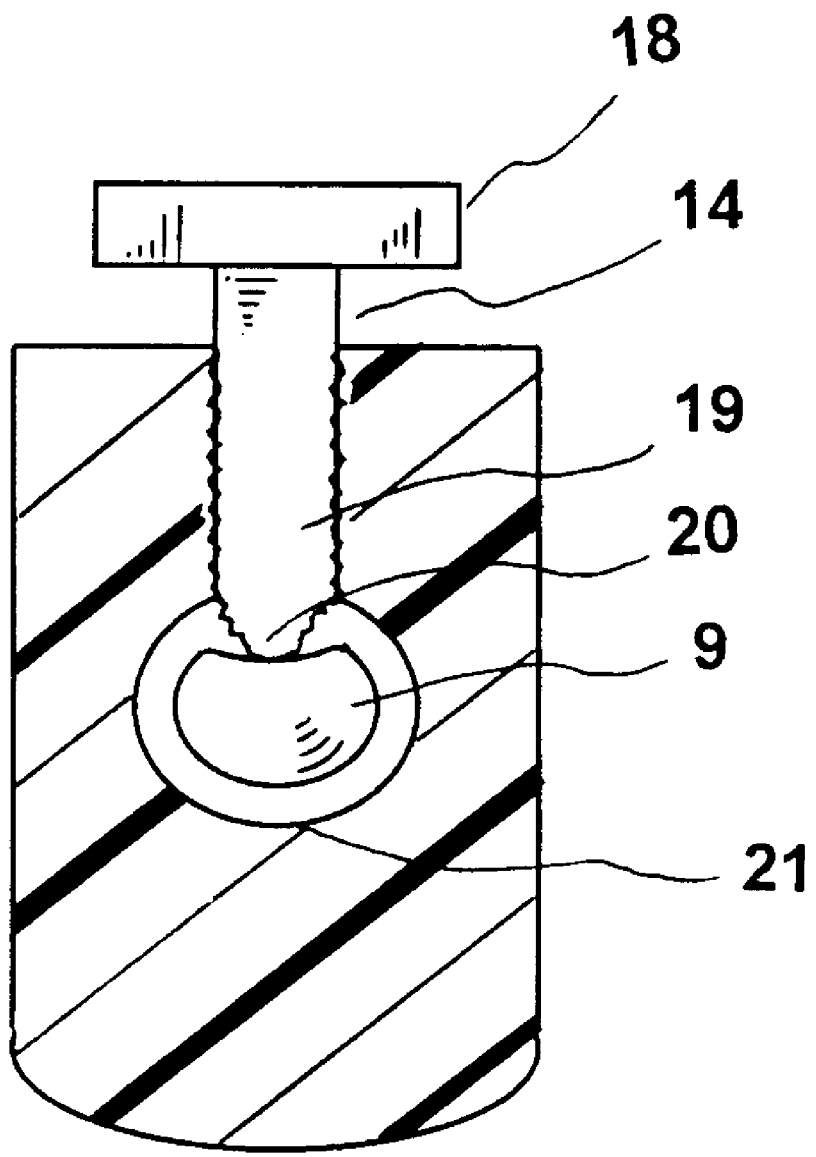
FIG. 2 is a cross-sectional view of the securing means for applying the pressure therapy to the medical device in FIG. 1.

FIG. 2 shows a cross-sectional view of the securing mechanism 14 for applying the pressure therapy to a medical device of the present invention. The securing mechanism 14 comprises a turning knob 18 and a forwarding screw or spring 19, wherein the end 20 of the screw or spring 19 can push the second elongate tubular shaft 9 against the receptacle 21 and secure the shaft in place. By loosening the screw 19, the second elongate tubular shaft 9 can freely move longitudinally, relative to the first elongate tubular shaft 1.

Figure 3:
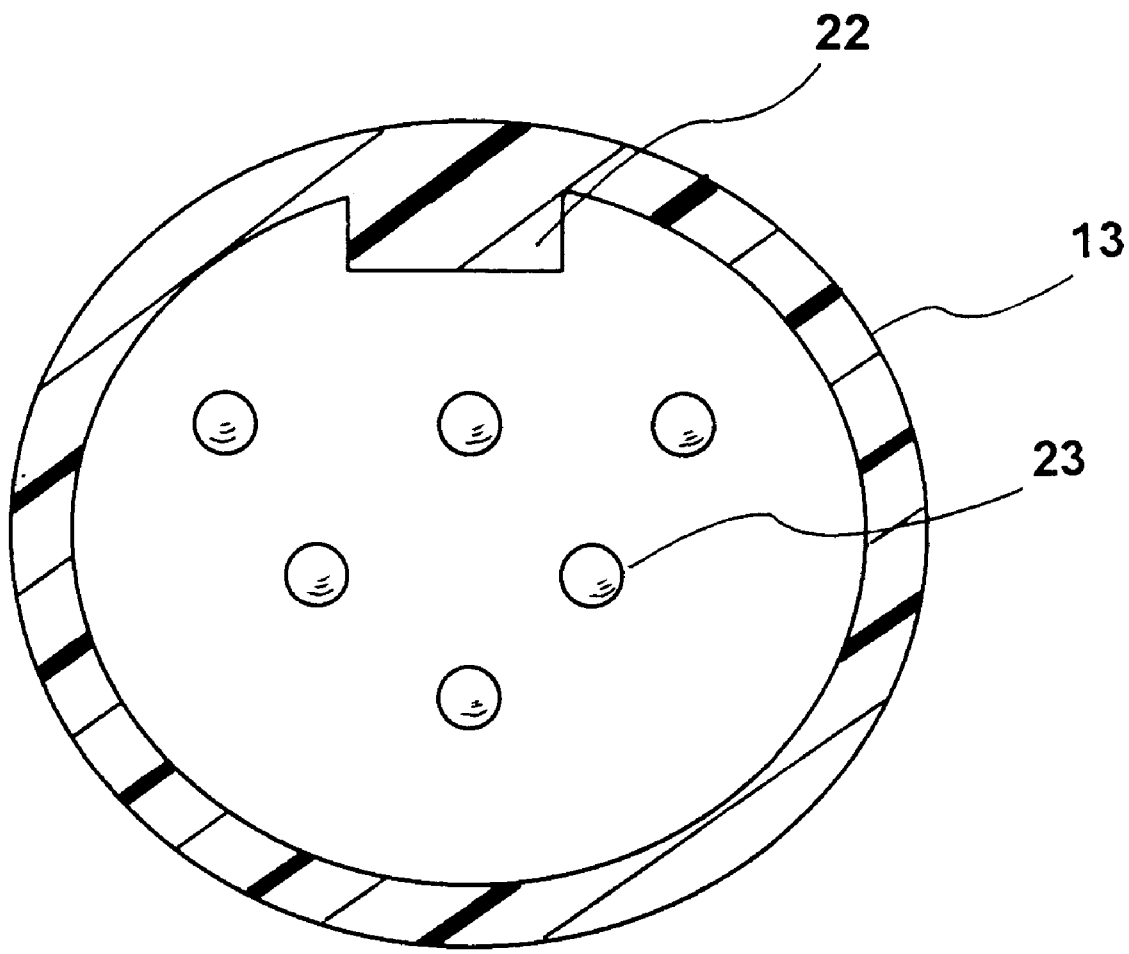
FIG. 3 is a front view of the connector means, section A—A, of FIG. 1.

FIG. 3 shows a front-end view of the connector means 13 of the present invention. The connector 13 comprises an orientation notch 22 and several pins 23 for connecting the electrical conductors 4 and 12, and temperature sensing wires 24 and 25 to external instruments, such as an ultrasonic energy generator, an EKG monitor, or a temperature control mechanism.

Figure 4:
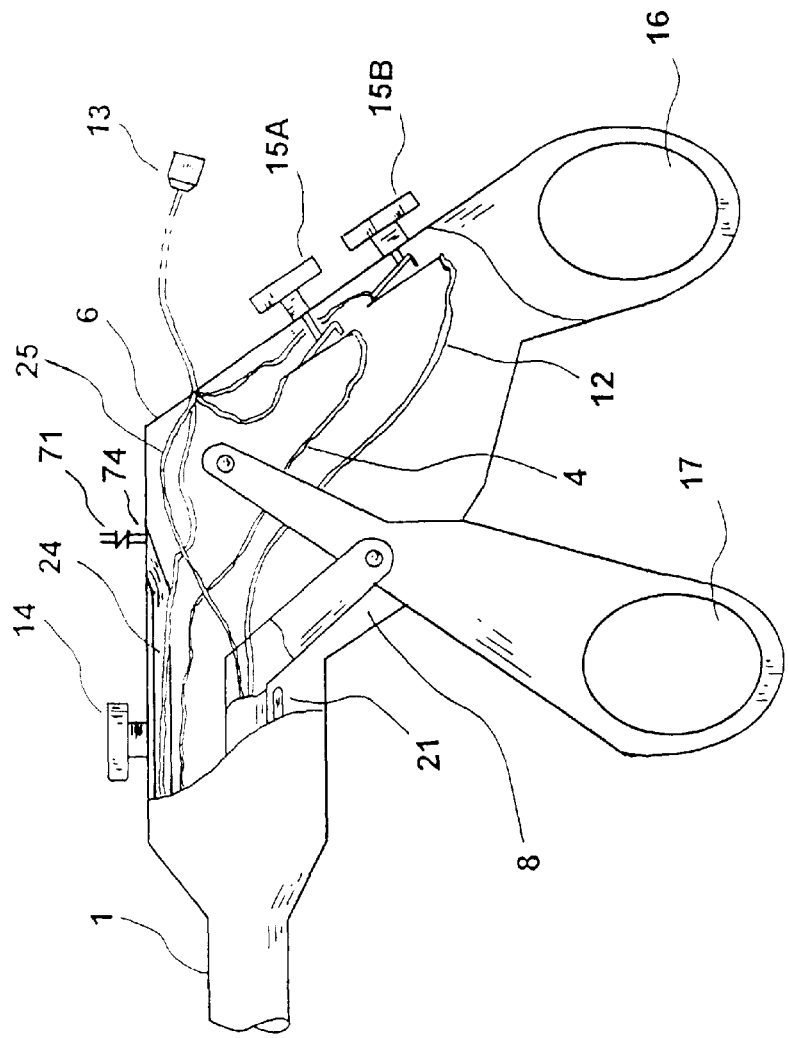
FIG. 4 is a cross-sectional view of the handpiece of FIG. 1.

FIG. 4 shows a cross-sectional view of the handpiece 6 of the present invention. The handpiece 6 comprises a cavity 8, and holders 16 and 17 for the thumb and finger so that the second elongate tubular shaft 9 can move longitudinally relative to the first elongate tubular shaft 1. The electricity of the electrical conductors 4 and 12 are controlled through on-off control knobs 15A and 15B to selectively deliver ultrasonic energy to either the first ultrasonic transducer 62 or the second ultrasonic transducer 63. The receptacle 21 is secured on the wall of the handpiece 6, which is used to assist the securing mechanism 14.

Figure 5:
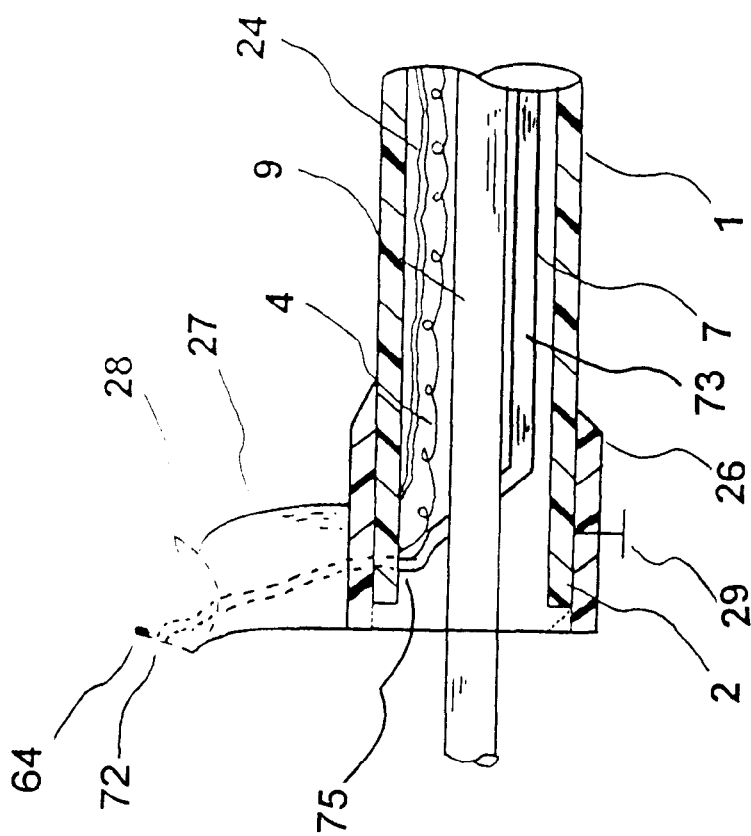
FIG. 5 is a side-view of a first clamp means having at least one first ultrasonic transducer mounted to a first tubular elongate shaft of the medical device.

The clamp means 3 is disposed at the distal end portion 2 of the first elongate tubular shaft 1. FIG. 5 shows a side-view of the mounting means for the first clamp means 3 having at least one ultrasonic transducer 62, mounted to a first tubular elongate shaft 1. The clamp means 3 comprises a base ring 26, a support 27, and a concave or convex circular element 28, which are all non-conductive, and at least one ultrasonic transducer 62 disposed on the surface of the circular element 28, wherein the base ring 26 is to fit into the distal end portion 2 of the first elongate tubular shaft 1.

In one embodiment, the ultrasonic transducer is in a needle-like shape, that points its needle-like end to the distal direction facing the target tissue. A stopper 30 at the distal end of the base ring 26 is in place to restrict and position the base ring 26 at the proper position on the shaft 1 when it is inserted and secured. The electrical conductor 4 is connected to the ultrasonic transducer 62 on the circular element 28. In one embodiment, the surface of the circular element 28 can be either flat, convex, concave, or with rough surface when facing the second clamp means 11. After fitting the clamp means 3 onto the distal end portion 2, a set screw 29 is used to securely maintain the clamp means 3 in place with respect to the first elongate tubular shaft 1.

Figure 6:
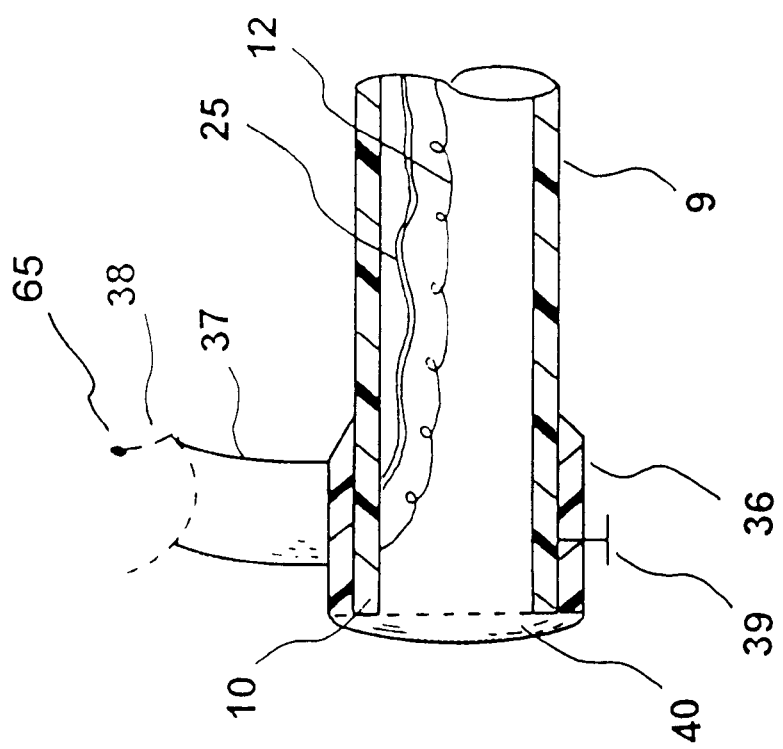
FIG. 6 is a side-view of a second clamp means having at least one second ultrasonic transducer mounted to a second tubular elongate shaft.

FIG. 6 shows a side-view of the mounting means for the second clamp means 11 mounted to a second tubular elongate shaft 9. The clamp means 11 is disposed at the distal end portion 10 of the second elongate tubular shaft 9. The clamp means 11 comprises a base ring 36, a support 37, and a circular element 38, which are all non-conductive, and at least one ultrasonic transducer 63 disposed on the surface of the circular element 38, wherein the base ring 36 is to fit into the distal end portion 10 of the second elongate tubular shaft 9. A stopper 40 at the distal end of the base ring 36 is in place to restrict and position the base ring 36 at the proper location on the shaft 9 when the base ring 36 is inserted and secured. The insulated electrical conductor 12 is connected to the ultrasonic transducer 63. In one embodiment, the surface of the conductive element 38 can be either flat, convex, concave, or with rough surface when facing the first clamp means 3. After fitting the clamp means 11 onto the distal end portion 10, a set screw 39 is used to securely maintain the clamp means 11 in place with respect to the second elongate tubular shaft 9. The needle-like end of the ultrasonic transducer 63 is positioned to face the target tissue.

In one embodiment, at least one temperature sensing means 64 or 65 is disposed close to the clamp means 3 or 11. Insulated temperature sensing wire means 24 and 25 passes from the temperature sensing means 64 and 65 at the distal end portion, to an external temperature control mechanism through an outlet connector 13. The ultrasonic energy delivery is controlled by using the measured temperature from the temperature sensing means 64 and/or 65, through a closed-loop temperature control mechanism and/or algorithm. When the measured temperature rises to the preset high-limit point, the temperature control mechanism sends out a signal to cut off the ultrasonic energy supply. In a similar manner, when the measured temperature drops to the preset low-limit point, the temperature control mechanism sends out a signal to activate the ultrasonic energy supply.

Figure 7:
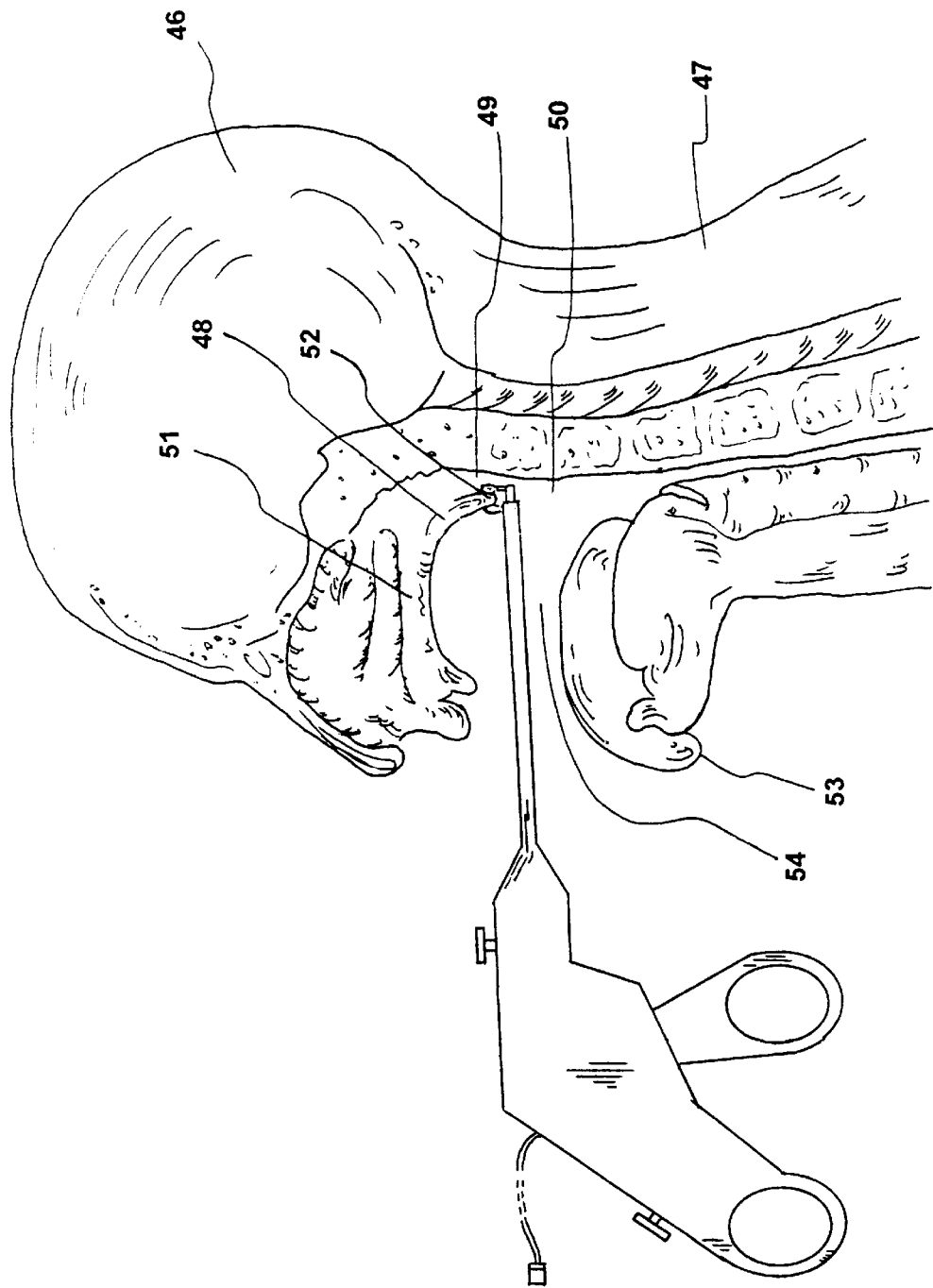
FIG. 7 shows a perspective view of a uvula region being treated by the medical device of the present invention.

FIG. 7 shows a perspective view of an uvula region being treated by the medical device of the present invention. For illustrative purposes, the median section of the head 46 and the neck region 47 is shown in FIG. 7. The soft palate 48 is a shelf of soft tissue which lies between the nasopharynx 49 and the oropharynx 50. It is attached in front to the posterior margin of the hard palate 51 and on either side to the deep surface of the superior constrictor muscles. Its posterior margin is free, and from its central part a conical process, called the uvula 52, hangs downwards. When the muscles of the soft palate are relaxed, the soft palate inclines downwards and backwards and is positioned concave downwards in both the coronal and sagital planes.

During procedures, the tongue 53 is pulled down to open the oral cavity 54. A tissue treatment method for reducing the size and mass of cellular tissues of the uvula in order to reduce snoring comprises the first step of inserting a medical device into the uvula of a patient, wherein the medical device comprises a first elongate tubular shaft, on which, thereof a first clamp means having at least one first ultrasonic transducer is mounted on a distal end portion, an electrical conductor passing through the shaft and connected to the first ultrasonic transducer, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within the lumen of the first elongate tubular shaft, the second elongate tubular shaft, on which, thereof a second clamp means having at least one second ultrasonic transducer, is mounted on a distal end portion, an electrical conductor passing through the shaft and connected to the second clamp means, and mounted on a proximal end portion of the shaft to the handpiece of the device, wherein the second elongate tubular shaft is moveable axially, relative to the first elongate tubular shaft; and an ultrasonic energy generating means, wherein the ultrasonic energy is supplied to either the first ultrasonic transducer, the second ultrasonic transducer, or to both ultrasonic transducer through electrical conductors. Contact the at least two ultrasonic transducer of the medical device against the cellular tissues of the uvula of a patient from its opposite sides. Activate the ultrasonic transducer to direct ultrasonic energy at the uvula tissue region to be treated, thereby generating thermal energy in the tissue. Heat the uvula tissue to a temperature and depth sufficient to ablate the uvula tissue, thereby reducing the size and mass of cellular tissues of the uvula in order to reduce snoring.

As an alternative illustration, a method of treating the tissues of a patient, the method comprises the steps of: (a) inserting a medical device into the opening of a patient, wherein the medical device comprises at least one ultrasonic transducer mounted on the distal end portion thereof; (b) positioning the medical device to place the at least one ultrasonic transducer in close proximity to a tissue region to be treated; (c) activating the ultrasonic transducer to direct ultrasonic energy at the target tissue region to be treated, thereby generating thermal energy in the tissue; and (d) heating the target tissue to a temperature and depth sufficient to ablate the tissue, thereby reducing the size and mass of cellular tissues.

Figure 8:
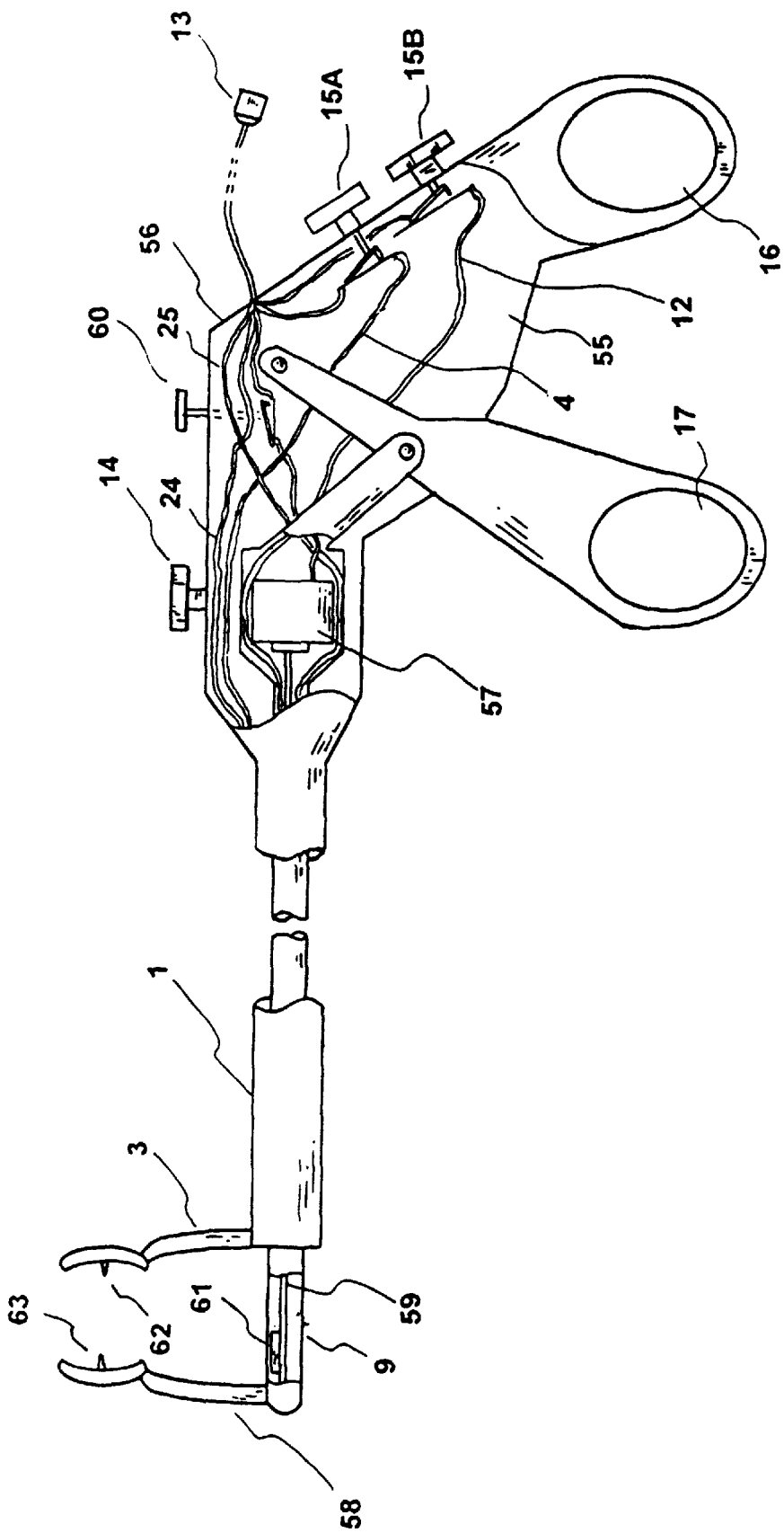
FIG. 8 is an over-all view of the medical device, having a plurality of ultrasonic transducer means, a clamp-type fixture, and an electric vibration means, constructed in accordance with the principles of the present invention.

FIG. 8 shows an over-all view of the medical device, having a pair of clamp means, a plurality of ultrasonic transducers, a clamp-type fixture for applying pressure to the target tissues, and an electric vibration means, constructed in accordance with the principles of the present invention. In addition to the above-described medical device, there is a cavity 55 inside the handpiece 56, in which a motor 57 is located. The second clamp means 58 which is mounted at the distal end portion of the second elongate tubular shaft 9 is connected to the handpiece 56 by a shaft 59. In one embodiment, a battery means (not shown), which is located at the proximal end of the cavity 55 of the handpiece 56, is used to supply the energy to the motor 59. In an alternate embodiment, the motor 59 is powered by an alternate current (AC) through a power input plug (not shown). In either case, the power supply is controlled by an on-off switch button 60 located conveniently on the handpiece 56. This alternate device has also the electrical conductors and temperature sensing wires as described in the above-described embodiment.

Attached to the shaft 59 there is an eccentric weight 61. The eccentric rotation of the weight 61 places the clamp means 58 into vibration via the shaft 59 due to the unbalancing effect of the eccentric weight 61. The vibrational amplitude of the clamp means 58 of the second elongate tubular shaft 9 is determined by the geometry of the shaft 59, the mass and configuration of the weight 61, and the rotational speed of the motor 57, among other factors.

In another embodiment, a fluid infusion means 71 is provided for the irrigation of a desired therapeutic agent, in either fluid phase or gel phase, to the uvula or to the target cellular tissue site. The fluid is adapted to diffuse out of the first elongate tubular shaft 1 at an opening 72 in close proximity of the ultrasonic transducer 62 on the circular member 28. The therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics and/or their mixtures. A passage 73 is provided inside the lumen of the first elongate tubular shaft 1 for transporting the fluid or gel from the proximal end 74 of the shaft 1 to the distal end 75. Thereafter the fluid or gel is diffused out of the device through the opening 72 over the exterior surface to provide a fluid protective layer surrounding the ultrasonic transducer to minimize temperature elevation of the ultrasonic transducer in contact with biological tissues.

The external ultrasonic energy generator means has the capability to supply ultrasonic energy by controlling the time, power, and temperature through an optional separate closed-loop temperature control means. The patient is connected to the ultrasonic energy generator means through a DIP electrode to form a closed-loop current system. Therefore, ultrasonic energy is applied and delivered to the targeted uvula region, through the ultrasonic transducers of this invention. The ultrasonic energy current in this invention is preferably within the range of 1 to 40 MHz. The electricity comprises applying at least 1 watt to the ultrasonic transducer. The frequency of the vibration of the medical device in this invention is preferably within the range of 60 to 1000 cycles per minute. By simultaneously applying ultrasonic energy to the ultrasonic transducers and by applying the pressure therapy, the uvula can be treated.

From the foregoing description, it should now be appreciated that a device system for the uvula and the treatment of tissues, comprising a suitable energy source and a pressure therapy, with an optional vibrational massage therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A tissue treatment method for reducing the size and mass of cellular tissues comprising the steps of:

(a) inserting a medical device into the uvula of a patient, wherein the medical device comprises a first elongate tubular shaft, on which, thereof a first clamp means having at least one first ultrasonic transducer is mounted on a distal end portion, an electrical conductor passing through the shaft and connected to the at least one first ultrasonic transducer, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within one lumen of the first elongate tubular shaft, the second elongate tubular shaft, on which, thereof a second clamp means having at least one second ultrasonic transducer is mounted on a distal end portion, an electrical conductor passing through the second elongate tubular shaft and connected to the at least one second ultrasonic transducer, and mounted on a proximal end portion of the shaft to the handpiece of the device, wherein the second elongate tubular shaft is moveable axially, relative to the first elongate tubular shaft; and an ultrasonic energy generating means, wherein the ultrasonic energy is supplied to either the first ultrasonic transducer, the second ultrasonic transducer, or to both ultrasonic transducers through electrical conductors;

(b) contacting the at least two ultrasonic transducers of the medical device against the cellular tissues of the uvula of a patient from its opposite sides;

(c) activating the ultrasonic transducer to direct ultrasonic energy at the uvula tissue region to be treated, thereby generating thermal energy in the tissue; and (d) heating the uvula tissue to a temperature and depth sufficient to ablate the uvula tissue, thereby reducing the size and mass of cellular tissues of the uvula in order to reduce snoring.

2. The treatment method as in claim 1, the step further comprising means for generating vibration at the distal end portion of the medical device, wherein the means for generating vibration at the distal end portion comprises a motor mounted in the cavity of the handpiece, which has a rotatable motor shaft, an elongate connecting shaft having a first end to which the distal end portion is connected, and a second end connected to the handpiece, a weight eccentrically mounted on the motor shaft with respect to the motor shaft axis, so as to rotate eccentrically, so that when the motor shaft rotates, the distal end portion of the medical device vibrates.

3. The treatment method as in claim 2, the step further comprising initiating the vibration to the distal end portion of the device to effect the vibrational therapeutic massage for treating the tissues.

4. The treatment method as in claim 1, the step further comprising the device having at least one temperature sensor, wherein the temperature sensor is disposed at close proximity of the ultrasonic transducer means of the first and/or the second tubular elongate shafts.

* * * * *